United States Patent
Voelker (10) Patent No.: US 8,300,906 B2
(45) Date of Patent: Oct. 30, 2012

(54) OPERATING SYSTEM HAVING AN OPERATING LAMP AND A CAMERA

(75) Inventor: Thomas Voelker, Hanau (DE)

(73) Assignee: Trumpf Medizin Systeme GmbH + Co. KG, Saalfeld (DE)

( * ) Notice: Subject to any disclaimer, the term of this patent is extended or adjusted under 35 U.S.C. 154(b) by 1384 days.

(21) Appl. No.: 11/940,821

(22) Filed: Nov. 15, 2007

(65) Prior Publication Data

US 2008/0285820 A1    Nov. 20, 2008

(30) Foreign Application Priority Data

May 15, 2007 (DE) ............... 20 2007 007 054 U (51) Int. Cl.
*G06K 9/00* (2006.01)
(52) U.S. Cl. .................. 382/128; 348/370; 396/14
(58) Field of Classification Search .................. 382/128
See application file for complete search history.

(56) References Cited

U.S. PATENT DOCUMENTS

| | | | |
|---|---|---|---|
| 3,588,488 A | 6/1971 | Lauterbach | |
| 3,930,149 A | 12/1975 | French | |
| 4,196,460 A | 4/1980 | Schreckendgust | |
| 4,380,794 A | 4/1983 | Lawson | |
| 4,757,426 A | 7/1988 | Scheller | |
| 6,488,390 B1 | 12/2002 | Lebens et al. | |
| 6,495,964 B1 | 12/2002 | Muthu et al. | |
| 6,880,957 B2 | 4/2005 | Walters | |
| 7,465,065 B2 * | 12/2008 | Marka | 362/232 |
| 7,614,763 B2 * | 11/2009 | Leibinger et al. | 362/235 |
| 2001/0021108 A1 | 9/2001 | Shimada et al. | |
| 2002/0048177 A1 | 4/2002 | Rahm et al. | |
| 2003/0165055 A1 | 9/2003 | Scholz | |
| 2003/0185009 A1 | 10/2003 | Walters | |
| 2005/0174473 A1 * | 8/2005 | Morgan et al. | 348/370 |
| 2005/0231945 A1 | 10/2005 | Leibinger et al. | |
| 2006/0251408 A1 * | 11/2006 | Konno et al. | 396/14 |

FOREIGN PATENT DOCUMENTS

| | | |
|---|---|---|
| DE | 19838627 | 3/2000 |
| DE | 10034594 | 3/2002 |
| DE | 10216645 | 11/2003 |
| EP | 1568936 | 8/2005 |
| EP | 1722157 | 11/2006 |
| WO | WO 00/35402 | 6/2000 |
| WO | WO 01/36864 | 5/2001 |
| WO | WO 03/019072 | 3/2003 |
| WO | WO 03/096761 | 11/2003 |

OTHER PUBLICATIONS

"Metalldampflampe", from Wikipedia, Jan. 7, 2007, 2 pages, http://de.wikipedia.org/wiki/Metalldampflampe—English equivalent is "Gas-discharge Lamp", also from Wikipedia, http://en.wikipedia.org/wiki/Gas-discharge_lamp.

* cited by examiner

*Primary Examiner* — Phillip A Johnston
(74) *Attorney, Agent, or Firm* — Fish & Richardson P.C.

(57) ABSTRACT

A method is described for displaying an image of an illumination field of a medical operation. The method includes recording an image at an illumination field of an operation, receiving a color temperature signal representative of an operating lamp that illuminates the illumination field of the operation, based on the received color temperature signal, adjusting parameters to compensate for differences in the received color temperature signal from white balance to produce a white balanced image, and outputting the white balanced image to a monitor.

27 Claims, 6 Drawing Sheets

OPERATING SYSTEM HAVING AN OPERATING LAMP AND A CAMERA

CROSS REFERENCE TO RELATED APPLICATION

This application claims priority under 35 U.S.C. §119(a) to German Application No. 20 2007 007 054.3, filed on May 15, 2007, the entire contents of which are hereby incorporated by reference.

TECHNICAL FIELD

The invention relates to a system including an operating lamp whose color temperature can be adjusted using a controller, and a camera for recording the operation that is illuminated by the operating lamp.

BACKGROUND

Digital cameras generally include a light-sensitive sensor, on which an image is imaged by means of optics. The incident light is converted into a charge in the sensor (for example, a charge-coupled device (CCD) sensor or a CMOS sensor), which is converted into a voltage value at a further stage. The voltage generated in this fashion is proportional to the incident quantity of light.

For detecting and representing a color image, the individual colors are detected selectively. For example, a three-chip camera can be used to separate the light into the corresponding red, green, and blue components with a beam splitter prism. The three-chip camera includes three sensors (or chips). Each of the beams separated from the prism is guided to a separate sensor, and each of the sensors represents the red, green, and blue components, respectively, of the incident light as separate voltage signals.

As another example, a one-chip camera can be used to detect a color image. The one-chip camera includes only one sensor (or chip); therefore, the color-selective detection of the incident light is obtained by color filters disposed on the pixels. In this fashion, different, microscopically small filters are disposed on the individual pixels, thus ensuring that each pixel is exposed to only one defined color component. In the one-chip camera, neighboring pixels are provided with different color filters in order to be able to regenerate the actual color of the image area in a downstream processing step. The downstream electronics calculates a color value for the respective area from the color components of the directly neighboring pixels.

The color temperature of operating lamps can be adjusted to improve the distinguishability of different types of tissue. The white light then tends to have components in a range from red to blue. If a video camera were used to transmit the image from the operating area, the resulting image would have a reddish to bluish color in dependence on the setting of the operating lamp.

SUMMARY

In one general aspect, an operating system includes an operating lamp for illuminating an illumination field of a medical operation, and a camera for recording an image at the illumination field. The operating lamp has a color temperature that is adjustable using a controller. A signal indicating the color temperature of the operating lamp is transmitted to the camera.

Implementations can include one or more of the following features. For example, the camera can be connected to the controller of the operating lamp through a data line. The color temperature signal can be transmitted from the controller to the camera.

The system can include a sensor that is configured to detect the color temperature at the illumination field. The color temperature signal can be transmitted from the sensor to the camera. The sensitivity of the sensor can be adjustable.

The camera can include memory for storing the color temperature signal. The camera can be housed in a handle of the operating lamp. The camera can be disposed on a support arm of the operating lamp. The camera can be integrated in a light module of the operating lamp.

The color temperature signal can be transmitted cyclically to the camera. The color temperature signal can be transmitted to the camera after the color temperature is adjusted by the controller.

The camera can adjust parameters to compensate for differences in the color temperature signal from white balance to produce a white balanced image.

The system can include a monitor connected to the camera to receive the white balanced image from the camera and to display the white balanced image.

In another general aspect, a method of performing a medical operation on living tissue is described. The method includes illuminating the tissue with an operating lamp that has a color temperature, adjusting the color temperature of the operating lamp with a controller, recording an image of the tissue with a camera, and transmitting a signal representing the color temperature of the operating lamp to the camera.

Implementations can include one or more of the following features. For example, the method can also include outputting a white balanced image from the camera to the monitor. The color temperature signal can be transmitted to the camera from the controller.

The color temperature signal can be transmitted to the camera from a sensor that is configured to detect the color temperature at the illumination field. The sensitivity of the sensor can be adjustable.

The method can also include storing the color temperature signal in the camera.

The color temperature signal can be transmitted cyclically to the camera. The color temperature signal can be transmitted to the camera after the color temperature is adjusted by the controller.

In another general aspect, a method is described for displaying an image of an illumination field of a medical operation. The method includes recording an image at an illumination field of an operation, receiving a signal representative of a color temperature of an operating lamp that illuminates the illumination field of the operation, based on the received color temperature signal, adjusting parameters to compensate for differences in the received color temperature signal from white balance to produce a white balanced image, and outputting the white balanced image to a monitor.

Implementations can include one or more of the following features. For example, receiving the signal representative of the color temperature can include receiving the color temperature signal from a controller of the operating lamp. Receiving the signal representative of the color temperature can include receiving the color temperature signal from a sensor that is configured to detect the color temperature at the illumination field.

The method can also include storing the color temperature signal.

Receiving the color temperature signal can include cyclically receiving the color temperature signal. Receiving the color temperature signal can include receiving the color temperature signal after the color temperature is adjusted by a controller of the operating lamp.

In general, the camera in the operating system described herein performs automatic white balance of the image from the operating area. The operating system therefore includes a means for transmitting the (adjusted) color temperature (that is, a signal that represents the color temperature of the operating lamp) to the camera. The information about the color temperature of the operating lamp (or the color temperature at the operating area) is transmitted to the camera. The camera can correspondingly adjust its white balance parameters.

For application in the field of the lamp family, described, e.g., by EP 1722157 A1, the color temperature is generated by the different weighting with light sources emitting different spectra. The process control that initiates this weighting has this information. These processors therefore precisely control the color temperature to be emitted from the operating lamp.

The color temperature (and therefore any adjustments of the color temperature) of the operating lamp are thus known and can be transmitted to electronics within the camera through an interface/data line. The camera receives the signal representing the color temperature and can adjust its internal balancing characteristic in correspondence with these values. This ensures direct adjustment of the camera to the color temperature at the operation area, thereby guaranteeing true-color reproduction of the imaged operating area.

The operating lamp has illuminants of different colors, and the operating lamp can change the color temperature within a range from about 3500K to about 5000K. When the color temperature changes, the light intensity of the operating lamp and the color reproduction remain almost constant. When the color temperature changes, the light intensity of the operating lamp remains constant.

The illuminants of the operating lamp and their drive units are calibrated such that the color temperature target specifications of the control exactly correspond with the actual values.

The color temperature (which can be an adjusted color temperature) is transmitted to the camera, either cyclically or only in case of a change, via serial connection (such as an RS485 bus) via a special protocol or by means of another data transfer. The camera includes a means for storing the values relating to sensitivity or amplification of the sensor portions for the individual colors. The values stored in the camera are then fetched by means of information from the operating lamp, and processing of the sensor signals is correspondingly driven.

The adjusted or emitted color temperature can alternatively be detected by a sensor and then be transmitted to the camera. The sensor can be integrated in the camera. The sensitivity of the color temperature sensors can alternatively be adjustable in order to improve detection of different colors. In this connection, it is, e.g., possible to distinguish tissue with increased blood supply (e.g., tumor cells) from tissue with less blood supply. The setting of the sensitivities can be stored either in fixed steps or can be continuous.

Further advantages of the invention can be extracted from the description and the drawings. The features mentioned above and below can be utilized individually or collectively in arbitrary combination. The embodiments shown and described are not to be understood as exhaustive enumeration but have exemplary character for describing the invention.

DETAILED DESCRIPTION

Figure 1:
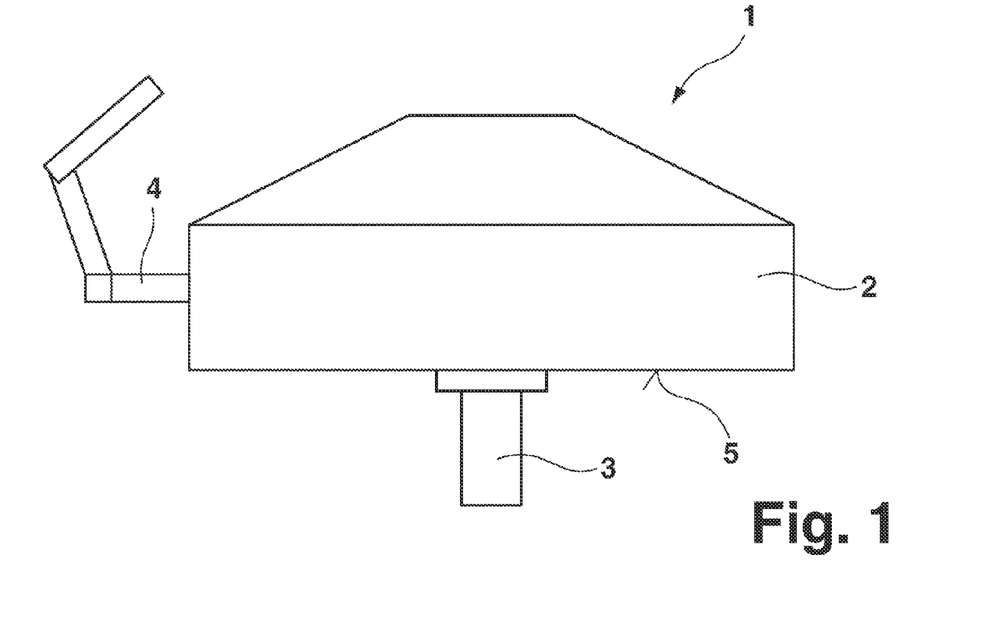
FIG. 1 is a schematic diagram of an operating lamp.

Referring to FIG. 1, an operating lamp 1 includes a lamp body 2 having an inner space that houses a light source. The lamp 1 is an "operating" lamp in this it is used to illuminate a medical procedure. The output of the operating lamp 1 can be controlled by the surgeon who performs the medical procedure to ensure suitable light during or throughout the medical procedure.

The lamp body 2 can be mounted on a support arm (such as a holder on a ceiling or wall of a building or mobile unit), such that it can be pivoted using a pivot arm of the support arm (an element 4 of which is shown in FIG. 1). The operating lamp 1 can be moved and pivoted in three dimensions. Additionally, the lamp 1 includes a handle 3 mounted to the lamp body 2 to permit positioning of the operating lamp 1 at any location above an operating table. The handle 3 can be detachably disposed on a lower side 5 of the operating lamp 1. Light is emitted on the lower side 5 of the lamp 1 to illuminate the location to be operated on.

Figure 2:
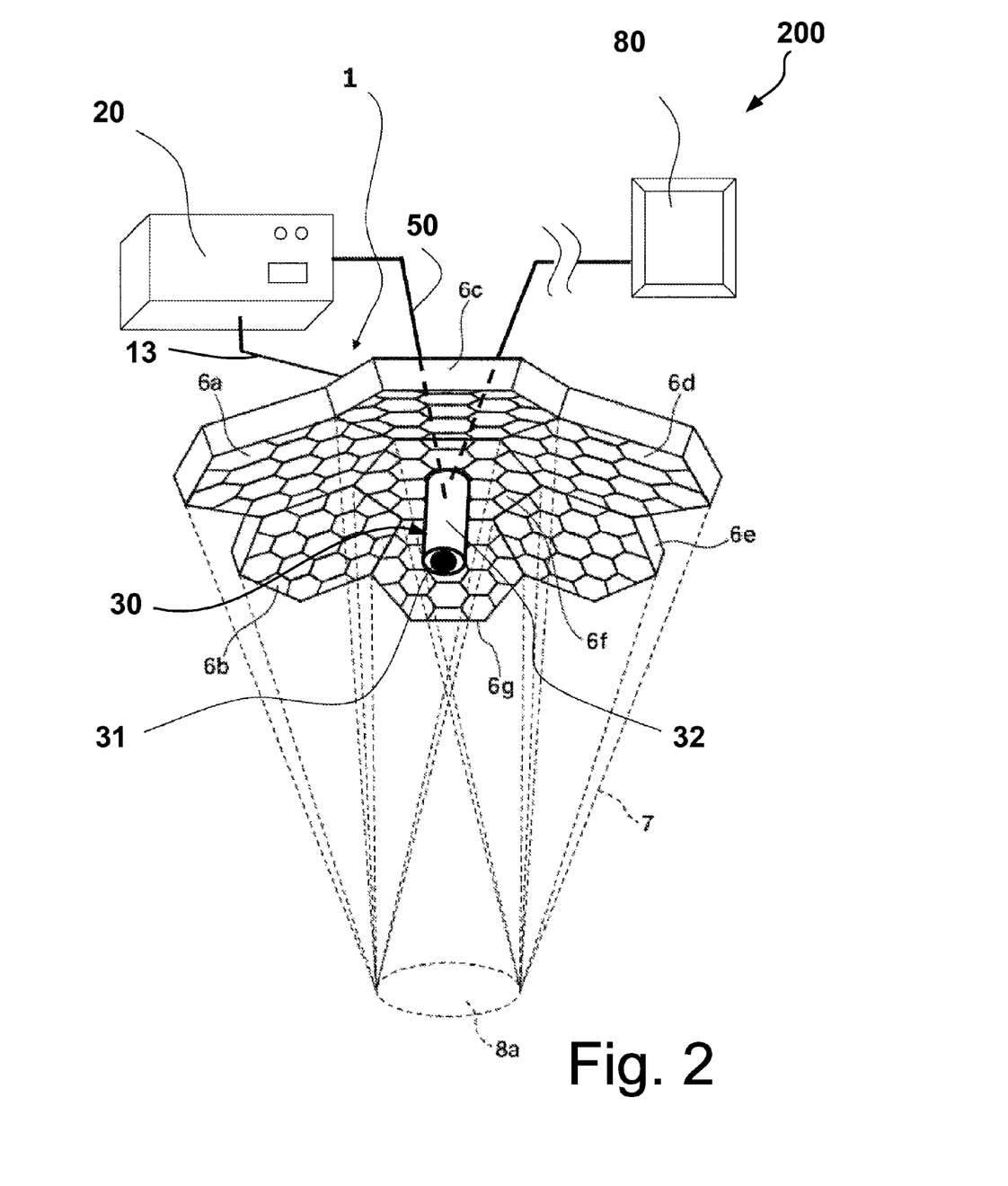
FIG. 2 is a schematic diagram of a first system including an operating lamp and a camera.

FIG. 2 shows an operating system 200 that incorporates the operating lamp 1. The operating lamp 1 includes individual light modules 6a-6g that are assembled to form a light source. The light produced by the light modules 6a-6g is indicated through broken lines by light beams 7, which generate a field of illumination 8a. The field of illumination 8a can be the surface on the operating table that is illuminated. The light from the light modules 6a-6g can be combined to form various light sources such that the size, shape, and intensity of the illumination field 8a can be changed depending on the combination of light modules 6a-6g.

Figure 3:
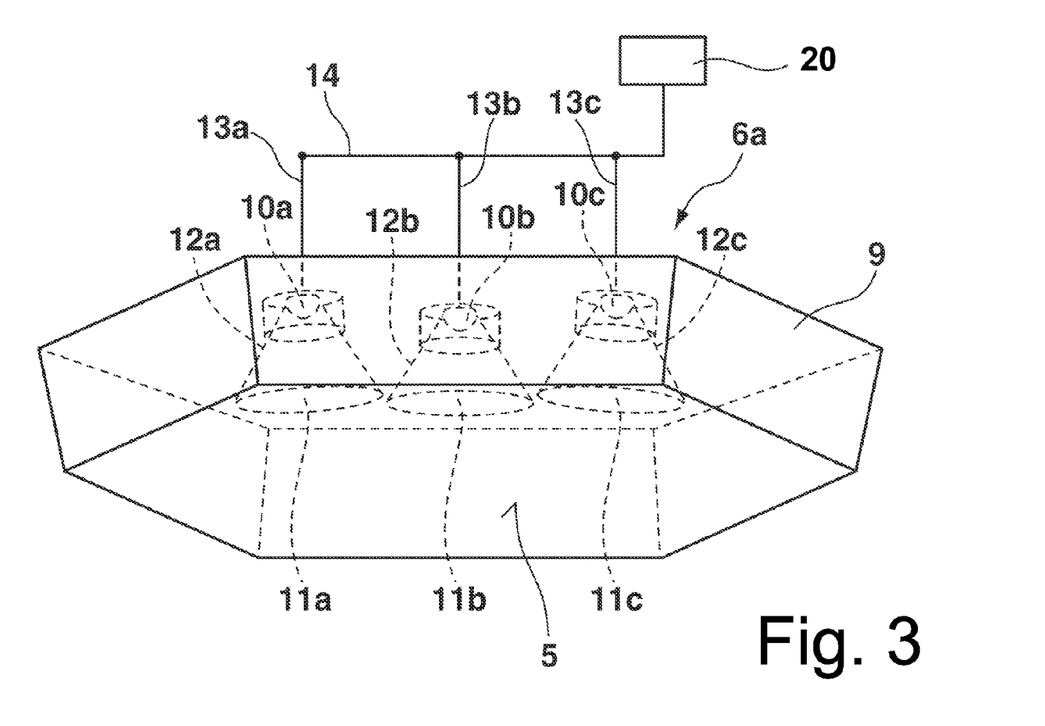
FIG. 3, is a schematic diagram of a light module that can be used in the operating lamp of FIG. 1, 2, 4, or 5.

Referring also to FIG. 3, an individual light module 6a includes a housing 9, the side surfaces of which have mechanical, electronic, and also electric connecting elements or connectors for driving illuminants in the light modules and connecting them to an electric power supply. The side surfaces can enable connection of the light module 6a with a neighboring light module 6c, 6f, or 6b. The light modules 6a-6g can be shaped so that they can be disposed on a spherical surface of a typical radius of 1000 mm without forming gaps between the light modules 6a-6g. Additionally, the optical axis of each light module 6a-6g can generally face the focus of the spherical surface. The light modules 6a-6g each include illuminants such as light emitting diodes (LEDs), halogen lamps, gas discharge lamps, incandescent lamps, and liquid crystals. As shown in FIG. 3, for example, the light module 6a includes three LEDs 10a-10c, each of which is associated with an optical element 11a-11c (such as a lens element) to produce respective light beams 12a-12c. It is possible to generate different illumination field shapes by disposing modules next to each other with changed angle of incidence. Intermediate elements such as the optical elements 11a-11c can be used for this purpose.

Each light module 6a-6g has several, for example, 30 to 50, uniformly distributed LEDs. In order to ensure that the light is emitted in two dimensions, the optical path of the LEDs that emit light in an almost point shape is widened to the light emitting surface at the lower side 5 by the optical elements, and the optical path is guided from there into the illumination field. Towards this end, each LED is associated with the optical element.

The light modules 6a-6g can be coupled to each other at any side surface, such that any combination is feasible. Therefore, it is possible to generate a lamp 1 whose illumination field is adjusted to the operation to be performed. FIG. 2 shows one example of adjusting the light modules 6a-6g in order to adjust the illumination field 8a through the light beams 7. Depending on the combination of the light modules 6a-6g, the illumination field 8a can have a larger longitudinal extension or a larger width. The illumination field 8a can be differently formed at its edges or in its center. This means that the illumination field 8a reflects the contour of the light module combination. Each individual light module 6a can illuminate a complete operating location. The light modules 6a-6g can be arbitrarily combined with further light modules to form the most different overall modules as the light source. This changes the size of the illumination field, the illumination intensity, and the shape of the illumination field 8a.

The light modules 6a-6g need not be rigidly connected to each other; instead, the light modules 6a-6g are pivotably coupled to each other by way of articulated links. These links render the light modules 6a-6g pivotable, such that the surfaces at the lower side 5, where the light is emitted, can be folded towards each other.

In addition to or as an alternative to providing hinge-like joints at respective connecting lines of the light modules 6a-6g, ball joints can be provided in one or more of the six corners of the light modules 6a-6g. The joints permit later adjustment of the position of previously combined light modules 6a-6g relative to each other. In addition thereto, the operating surgeon can vary the illumination fields.

The individual light modules 6a-6g form together a light source with a color temperature of approximately 3500 K to 5000 K, and a color reproduction index Ra>93 in order to obtain a natural representation of the color, e.g., of the tissue to be operated on. For this reason, in addition to LEDs (such as, for example, LED 10a in light module 6a) generating white light, other LEDs (such as, for example, LEDs 10b, c) generating color light are used. A drop in the spectrum that would happen if only white LEDs were used, is prevented by admixing color light components such as cyan and blue. With a constant brightness of the white LEDs (for example, LED 10a), the color temperature and color reproduction of the mixed light generated by the light source consisting of all individual light modules 6a-6g can be variably adjusted through exclusively continuous dimming of the intensity of the color LEDs (for example, LEDs 10b and 10c). The luminous flux intensity of the color LEDs can be continuously changed.

The LEDs (such as LEDs 10a, 10b, 10c) are connected to a controller 20 through power supply lines 13 (for example, through lines 13a, 13b, 13c shown in FIG. 3), which permits electric dimming of the luminous flux of the LEDs. Electric dimming of the color LEDs (for example, LEDs 10b and 10c) results in a change or adjustment of color temperature and/or the color reproduction, which is advantageous for illuminating the operating location. It is thereby feasible for the operating surgeon to utilize the adjustability in such a fashion that he/she mixes color light and white light in dependence on his/her requirements in order to highlight special tissue types or tissue changes in a light-specific fashion. This makes it easier for the operating surgeon to identify individual tissue types or tissue changes.

It is possible to set a basic color temperature of 4500 K that is automatically generated when the operating lamp 1 is switched on. The operating surgeon can individually adjust other desired color temperatures with the aid of a control panel or a keyboard of the controller 20 in dependence on the application of the operating lamp. The required adjustment parameters can be stored in a storage of the controller 20. In another feasible variant, the operating surgeon can additionally store further settings chosen by him/her, and also change these settings at a later time.

The operating system 200 includes a camera system 30 having a camera 31 and a housing 32. The camera system 30 can be mounted in one of one of the light modules, i.e., the central light module 6f of the operating lamp 1 can bear the camera system 30. The camera 31 can be a video camera or a still photography camera. Additionally, the camera 31 can be configured to record either or both still images and videos.

When the camera system 30 is inserted into the central light module 6f, the required electrical connections and the connections suitable for image processing are automatically established between the camera system 30 and other components through a data line 50. The camera housing 32 can be the handle 3 of the operating lamp 1 so that the camera 31 is mounted within the operating lamp 1 handle 3.

The camera system 30 should be positioned so that it has a view of the operating area (that is, from the illumination field 8a) so that the camera system 30 can transmit an image from the operating area. The camera system 30 is connected to a monitor 80 that is positioned in the operating room or at any other location, such as, e.g., an auditorium, conference rooms, or offices of physicians who are online.

In one implementation, the camera 31 is connected to the controller 20 of the operating lamp 1. The camera 31 can be a one-chip, three-chip, or any suitable digital camera that produces color. The color temperature of the operating lamp 1 can be automatically transmitted to electronics within the camera 31 through the data line 50 and from the controller 20 (which stores the color temperature).

The data can be transmitted to the camera 31 cyclically or only when a change in the color temperature occurs. The data can be transmitted by any suitable means of data transfer or protocol, such as, for example, through an RS 485 bus. The electronics within the camera 31 include a processor and memory for storing information for use by the processor. The memory stores values relating to the sensitivity or amplification of the sensor portions for the individual colors (where the sensor portions can be individual pixels or each chip, depending on whether the camera 31 is a one-chip or a three-chip camera. The memory can also store applications for operation by the processor. The camera 31 (and in particular, the electronics within the camera 31) receives the color temperature and adjusts its internal balancing characteristics relative to the color temperature. In this way, the camera 31 directly adjusts its output to the monitor 80 to be a true-color reproduction of the imaged operating area. Moreover, the parameters for white balance of the camera 31 can be correspondingly adjusted. White-balanced images can be displayed on the monitor 80.

It is also feasible to dispose the camera system 30 at any other location of the operating lamp 1.

Figure 4:
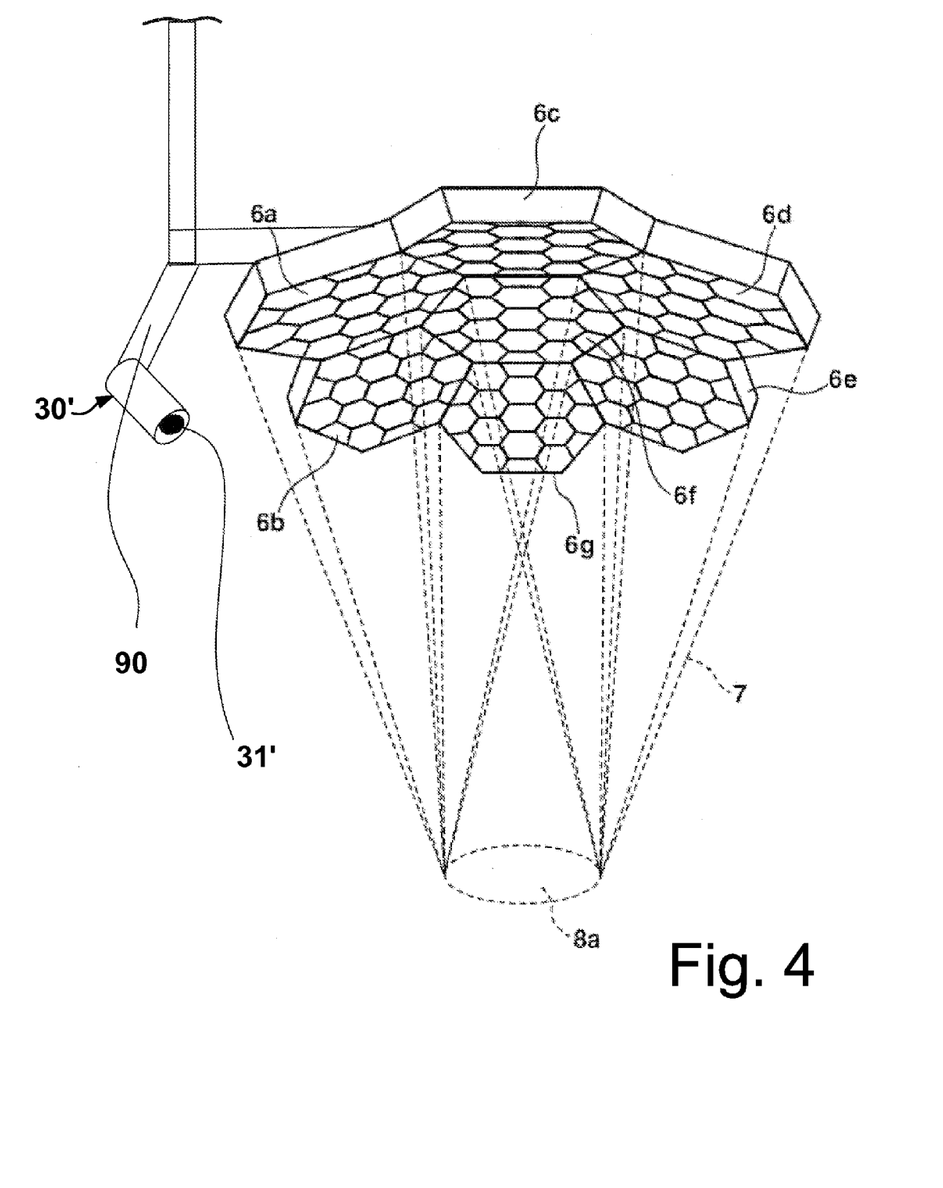
FIG. 4 is a schematic diagram of a second system including an operating lamp and a camera.

For example, as shown in FIG. 4, the camera system 30' including the camera 31' is provided on a support arm 90 of the operating lamp system.

Figure 5:
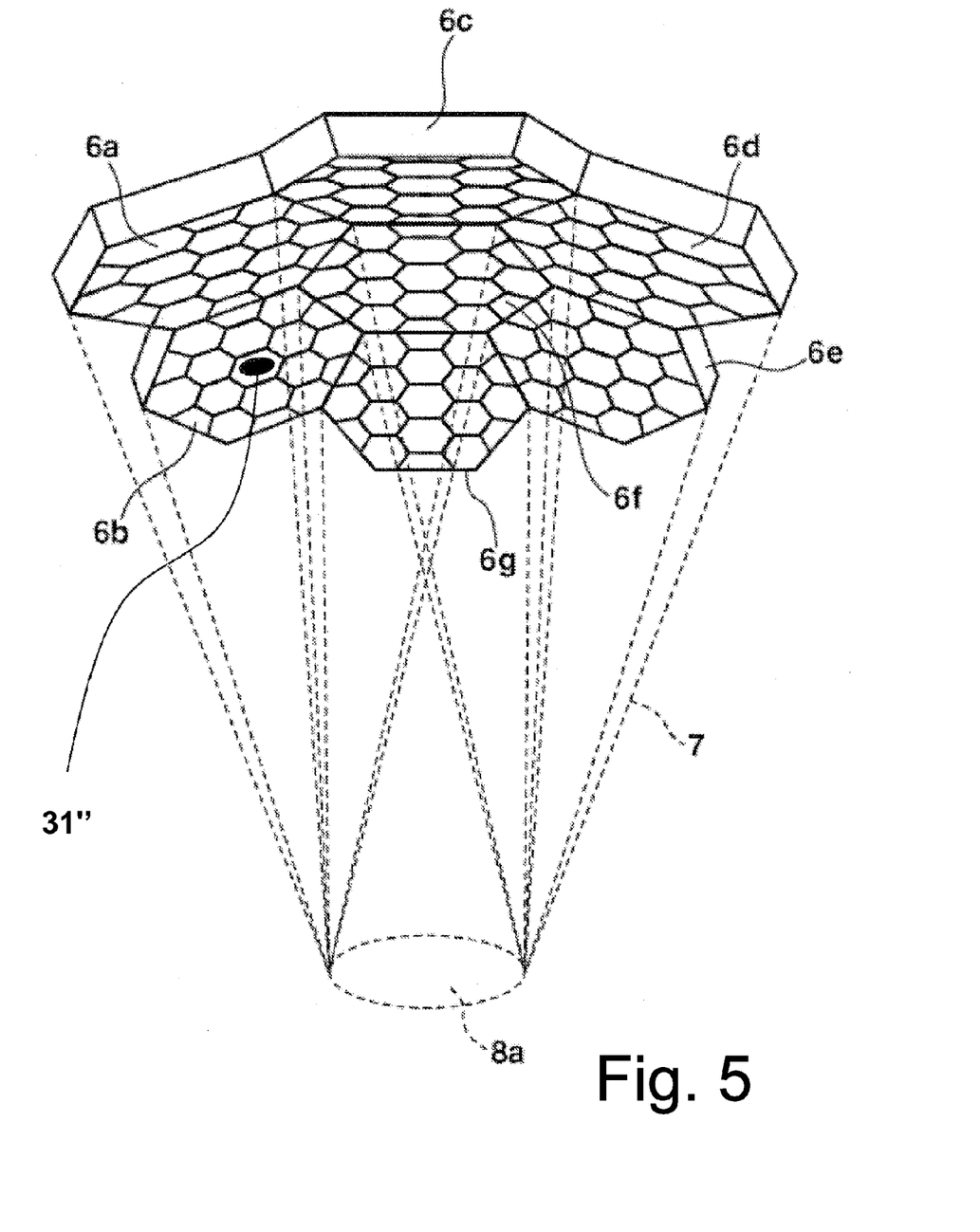
FIG. 5 is a schematic diagram of a third system including an operating lamp and a camera.

As another example as shown in FIG. 5, the camera 31" is integrated in a light module such as the light module 6b. For example, the camera 31" can be positioned at, near, or within the housing 9 and the electronics of the camera 31" can be within the housing 9.

Although not shown, the data line 50, the controller 20, and the monitor 80 (shown in FIG. 2) are coupled to the light modules and the camera system and the cameras in FIGS. 4 and 5.

Figure 6:
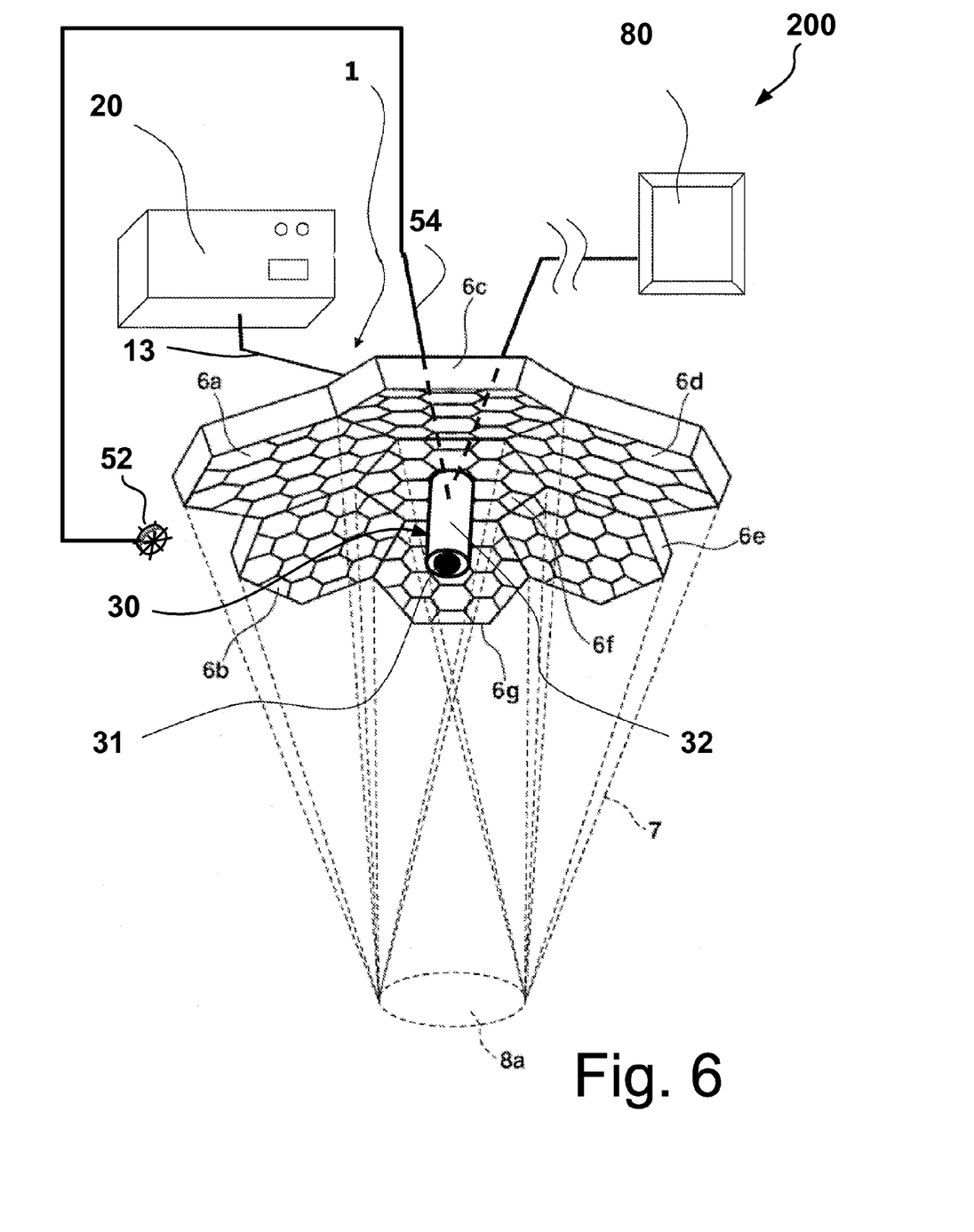
FIG. 6 is a schematic diagram of a fourth system including an operating lamp and a camera.

Referring to FIG. 6, in another implementation, the color temperature of the operating lamp 1 or the color temperature at the illumination field 8a can be detected by one or more sensors 52 and then transmitted to the camera 31 by a data line 54. In this implementation, therefore, the camera 31 need not acquire data directly from the controller 20. The one or more color temperature sensors 52 can be integrated within the camera system 30 or can be mounted external to the camera system 30 (as shown in FIG. 6). In any case, the sensors 52 are configured to view the illumination field 8a. The sensitivity of the one or more sensors 52 can be adjusted depending on the detection of certain colors. For example, the one or more sensors 52 can be configured to be sensitive enough to distinguish tissue with increased blood supply from tissue with less blood supply. The sensitivity can be adjusted either in fixed steps or continuously.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An operating system comprising:
   an operating lamp for illuminating an illumination field of a medical operation, wherein the operating lamp has a color temperature that is adjustable using a controller; and
   a camera for recording an image at the illumination field;
   wherein a signal indicating the color temperature at the illumination field is transmitted from the controller to the camera, and wherein the camera comprises memory for storing values relating to a sensitivity or amplification of sensor portions for individual colors.

2. The system of claim 1, further comprising a sensor that is configured to detect the color temperature at the illumination field.

3. The system of claim 2, wherein the color temperature signal is transmitted from the sensor to the camera.

4. The system of claim 2, wherein the sensitivity of the sensor is adjustable.

5. The system of claim 1, wherein the camera is housed in a handle of the operating lamp.

6. The system of claim 1, wherein the camera is disposed on a support arm of the operating lamp.

7. The system of claim 1, wherein the camera is integrated in a light module of the operating lamp.

8. The system of claim 1, wherein the color temperature signal is transmitted cyclically to the camera.

9. The system of claim 1, wherein the color temperature signal is transmitted to the camera after the color temperature is adjusted by the controller.

10. The system of claim 1, wherein the camera adjusts parameters to compensate for differences in the color temperature signal from white balance to produce a white balanced image.

11. The system of claim 10, further comprising a monitor connected to the camera to receive the white balanced image from the camera and to display the white balanced image.

12. A method of performing a medical operation on living tissue, the method comprising:
   illuminating the tissue with an operating lamp that has a color temperature;
   adjusting the color temperature of the operating lamp with a controller;
   transmitting a signal representative of the color temperature at an illumination field from the controller to a camera, wherein the camera comprises memory for storing values relating to a sensitivity or amplification of sensor portions for individual colors;
   adjusting white balancing parameters of the camera based on the signal; and
   recording a white balanced image of the tissue with the camera.

13. The method of claim 12, further comprising outputting the white balanced image from the camera to the monitor.

14. The method of claim 12, wherein the color temperature signal is a color temperature setting of the operating lamp and is transmitted to the camera from the controller.

15. The method of claim 12, wherein the color temperature signal is transmitted to the camera from a sensor that is configured to directly detect the color temperature at the illumination field.

16. The method of claim 15, wherein the sensitivity of the sensor is adjustable.

17. The method of claim 12, wherein the color temperature signal is transmitted cyclically to the camera.

18. The method of claim 12, wherein the color temperature signal is transmitted to the camera after the color temperature of the operating lamp is adjusted by the controller.

19. A method of displaying an image of an illumination field of a medical operation, the method comprising:
   recording an image at an illumination field of an operation that is illuminated by an operating lamp comprising a controller;
   receiving at a camera from the controller a signal representative of a color temperature at the illumination field of the operation, wherein the camera comprises memory for storing values relating to a sensitivity or amplification of sensor portions for individual colors;
   based on the received color temperature signal, adjusting white balancing parameters of the camera to compensate for differences in the received color temperature signal from a previously defined white balance to produce a white balanced image; and
   outputting the white balanced image to a monitor.

20. The method of claim 19, wherein receiving the signal representative of the color temperature includes receiving the color temperature signal from a sensor that is configured to detect the color temperature at the illumination field.

21. The method of claim 19, further comprising storing the color temperature signal.

22. The method of claim 19, wherein receiving the color temperature signal includes cyclically receiving the color temperature signal.

23. The method of claim 19, wherein receiving the color temperature signal includes receiving the color temperature signal after the color temperature is adjusted by a controller of the operating lamp.

24. An operating system comprising:
an operating lamp for illuminating an illumination field of a medical operation, wherein the operating lamp has a color temperature that is adjustable using a controller; and
a camera connected to the controller of the operating lamp through a data line for recording an image at the illumination field;
wherein a signal indicating the color temperature settings of the operating lamp is transmitted from the controller to the camera via the data line, and wherein the camera comprises memory for storing values relating to a sensitivity or amplification of sensor portions for individual colors.

25. An operating system comprising:
an operating lamp for illuminating an illumination field of a medical operation, wherein the operating lamp has a color temperature that is adjustable using a controller; and
a camera for recording an image at the illumination field,
wherein a signal indicating the color temperature at the illumination field, which is a signal of a color temperature setting of the operating lamp, is transmitted from the controller to the camera, the camera comprises memory for storing values relating to a sensitivity or amplification of sensor portions for individual colors, and white balancing parameters of the camera are adjusted based on the signal indicating the color temperature to compensate for differences in the color temperature signal to produce a white balanced image.

26. A method of performing a medical operation on living tissue, the method comprising:
illuminating the tissue with an operating lamp that has a color temperature;
adjusting the color temperature of the operating lamp with a controller;
recording an image of the tissue with a camera;
transmitting a signal representative of the color temperature at an illumination field from the controller to the camera, wherein the camera comprises memory for storing values relating to a sensitivity or amplification of sensor portions for individual colors; and
adjusting white balancing parameters of the camera to compensate for differences in the color temperature signal from a previously defined white balance to produce a white balanced image.

27. A method of displaying an image of an illumination field of a medical operation, the method comprising:
recording an image at an illumination field of an operation that is illuminated by an operating lamp comprising a controller;
receiving at a camera from the controller a signal representative of a color temperature at the illumination field of the operation, the signal comprising a color temperature setting of the operating lamp, wherein the camera comprises memory for storing values relating to a sensitivity or amplification of sensor portions for individual colors;
based on the received color temperature signal, adjusting white balancing parameters of the camera to compensate for differences in the received color temperature signal from white balance to produce a white balanced image; and
outputting the white balanced image to a monitor.

* * * * *